(12) United States Patent
Dales

(10) Patent No.: US 8,550,097 B2
(45) Date of Patent: Oct. 8, 2013

(54) DENTAL FLOSS HOLDER

(76) Inventor: Matthew William Dales, Toronto (CA)

( * ) Notice: Subject to any disclaimer, the term of this patent is extended or adjusted under 35 U.S.C. 154(b) by 0 days.

(21) Appl. No.: 13/304,357

(22) Filed: Nov. 24, 2011

(65) Prior Publication Data
US 2013/0133687 A1 May 30, 2013

(51) Int. Cl.
*A61C 15/00* (2006.01)
(52) U.S. Cl.
USPC .......................................................... 132/327
(58) Field of Classification Search
USPC ..................... 132/323, 324–327; D28/66, 67; 24/132 R
See application file for complete search history.

(56) References Cited

U.S. PATENT DOCUMENTS

| | | | |
|---|---|---|---|
| 4,622,986 A | 11/1986 | Harris et al. | |
| 4,638,824 A | 1/1987 | De La Hoz | |
| 5,199,452 A * | 4/1993 | Cheng | 132/325 |
| 5,454,386 A | 10/1995 | Dix | |
| 5,477,871 A | 12/1995 | Sanchez, Jr. | |
| 5,685,325 A * | 11/1997 | Wei et al. | 132/323 |
| 2004/0250834 A1 | 12/2004 | Bowsher | |

FOREIGN PATENT DOCUMENTS

CA          2560963          10/2004

\* cited by examiner

*Primary Examiner* — Rachel Steitz
(74) *Attorney, Agent, or Firm* — Bereskin & Parr LLP/S.E.N.C.R.L., s.r.l.

(57) ABSTRACT

A dental floss gripper has a ring-shaped base element and a clamp that is pivotally coupled to the ring for movement between open and closed positions. In the closed position, the clamp grips a length of dental floss supported on the external surface of the ring. The clamp and the ring are configured so that the clamp snap-fits to the base element and securely holds the dental floss in use.

6 Claims, 5 Drawing Sheets

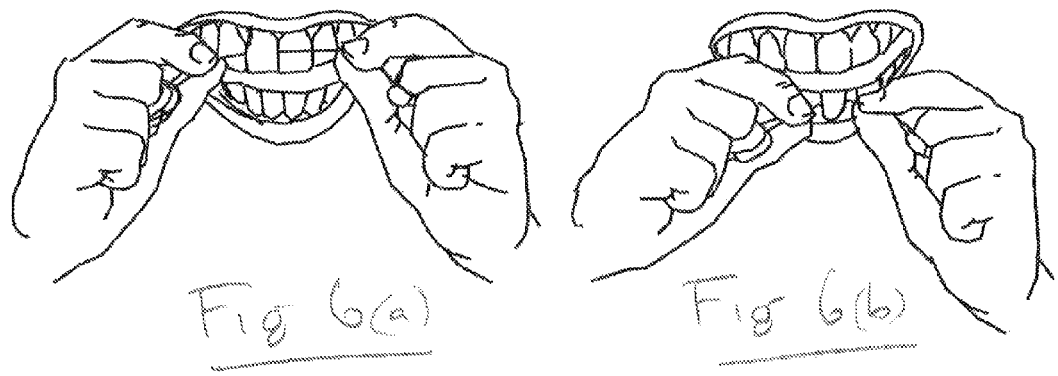
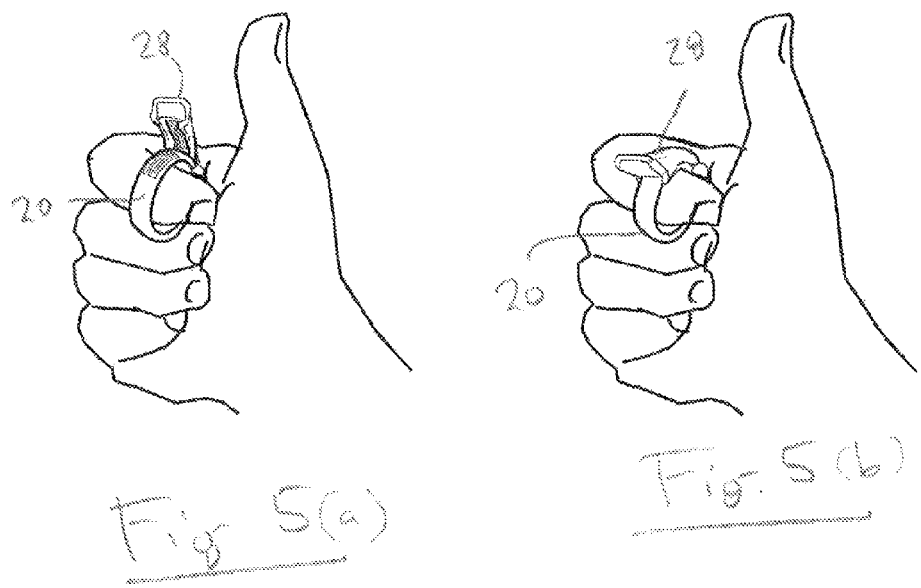

DENTAL FLOSS HOLDER

FIELD

This invention relates generally to the field of dental hygiene, and in particular to a device for gripping dental floss during use.

INTRODUCTION

Dental floss is recommended and quite widely used as part of a regime for good dental hygiene. Traditionally, a length of dental floss is held between a user's two hands with end portions of the dental floss wrapped around the index fingers of each hand, so that the dental floss can be held taut. The floss is then inserted between an adjacent pair of teeth and moved back and forth to remove accumulated material and stimulate the gums.

Using dental floss in this way can be awkward and cause a degree of discomfort. The portions of the dental floss that are wrapped around the fingers may tend to irritate or even cut into the skin. In order to address these issues, proposals have been made for holders between which a length of dental floss can be tensioned during use in flossing the teeth. The following prior art documents show some examples of dental floss holders and related products:

U.S. Pat. No. 4,622,986 (Harris et al.)
U.S. Pat. No. 4,638,824 (De La Hoz)
U.S. Pat. No. 5,454,386 (Dix)
U.S. Pat. No. 5,477,871 (Sanchez, Jr.)
U.S. Patent Application Publication No. US 2004/0250834 (Bowsher)
Canadian Patent Application No. 2,560,963 (Bowsher)

An object of the present invention is to provide a device that can be used to hold portions of a length of dental floss in a comfortable and convenient manner and without cutting into or otherwise irritating the fingers of a user.

SUMMARY

According to the present invention there is provided a dental floss gripper comprising a base element having an outer surface portion for supporting a length of dental floss, and a clamp pivotally coupled to the base element for movement between a closed position in which the clamp overlies said outer surface portion of the base element, and an open position. The base element and the clamp have confronting surfaces which co-operate to clamp the length of dental floss therebetween when the clamp is in the closed position. The clamp and base element are configured so that the clamp releasably snap-fits to the base element in moving to said closed position. In its open position, the clamp permits insertion and subsequent removal of a length of dental floss between the confronting surfaces. Ideally, a pair of dental floss grippers will be used, one to grip each end portion of the length dental floss.

The clamp of the relevant gripper is initially disposed in its open position. The end portion of the length of dental floss is placed between the confronting surfaces of the base element and clamp and the clamp is snapped into its closed position, gripping the dental floss. The user then holds one gripper in each hand and manipulates the length of dental floss extending between the grippers to perform the flossing procedure. At the end of the procedure, the clamp of each gripper can be simply "flipped" up to its open position allowing the length of dental floss to be adjusted or removed and discarded.

While the base element of the gripper could be designed, for example, to provide a hand grip that would fit in the palm of a user's hand, preferably the base element is a ring that is conveniently sized to receive a finger of a user. Typically, the ring may have an internal diameter of approximately 2 cm. The gripper may of course be made available in other sizes, or in a range of sizes.

The clamp preferably has an arcuate shape that corresponds generally to the curvature of the ring and is pivoted at one end to the ring itself. The clamp may be generally channel-shaped with opposite side walls of the channel embracing opposite side portions of the ring. The side walls of the channel and corresponding side portions of the ring may be shaped to provide the required snap-fitting of the clamp to the ring in the closed position.

The confronting surfaces of the ring and clamp may be formed to provide ribs or other protuberant formations that will mechanically grip the dental floss. In one embodiment, a series of ribs of generally triangular cross-section extend longitudinally of the relevant surface of the clamp and are spaced laterally of that surface. Corresponding areas on the ring are provided with ribs or with roughened or otherwise friction-engendering transverse surface portions that co-operate with the ribs on the clamp.

Preferably, the ring and clamp are made of an appropriate plastic material. Additives such as a silicone or latex may be included to enhance the gripping effect between the clamp and ring and/or to enhance comfort of the ring for the user.

DRAWINGS

In order that the invention may be more clearly understood, reference will now be made to the accompanying drawings which illustrate a particular preferred embodiment of the invention and in which.

FIG. 5 comprises views (a) and (b) that show the dental floss gripper in use on the index finger of a user, with the clamp respectively in the open and closed positions; and, FIG. 6 comprises views (a) and (b) showing the dental floss gripper in use.

DESCRIPTION OF VARIOUS EMBODIMENTS

The drawings show a dental floss gripper in accordance with a preferred embodiment of the invention which comprises a base element 20 having an opening 22 for receiving a finger of a user and an outer surface portion 24 for supporting a length of dental floss indicated at 26.

Figure 1:
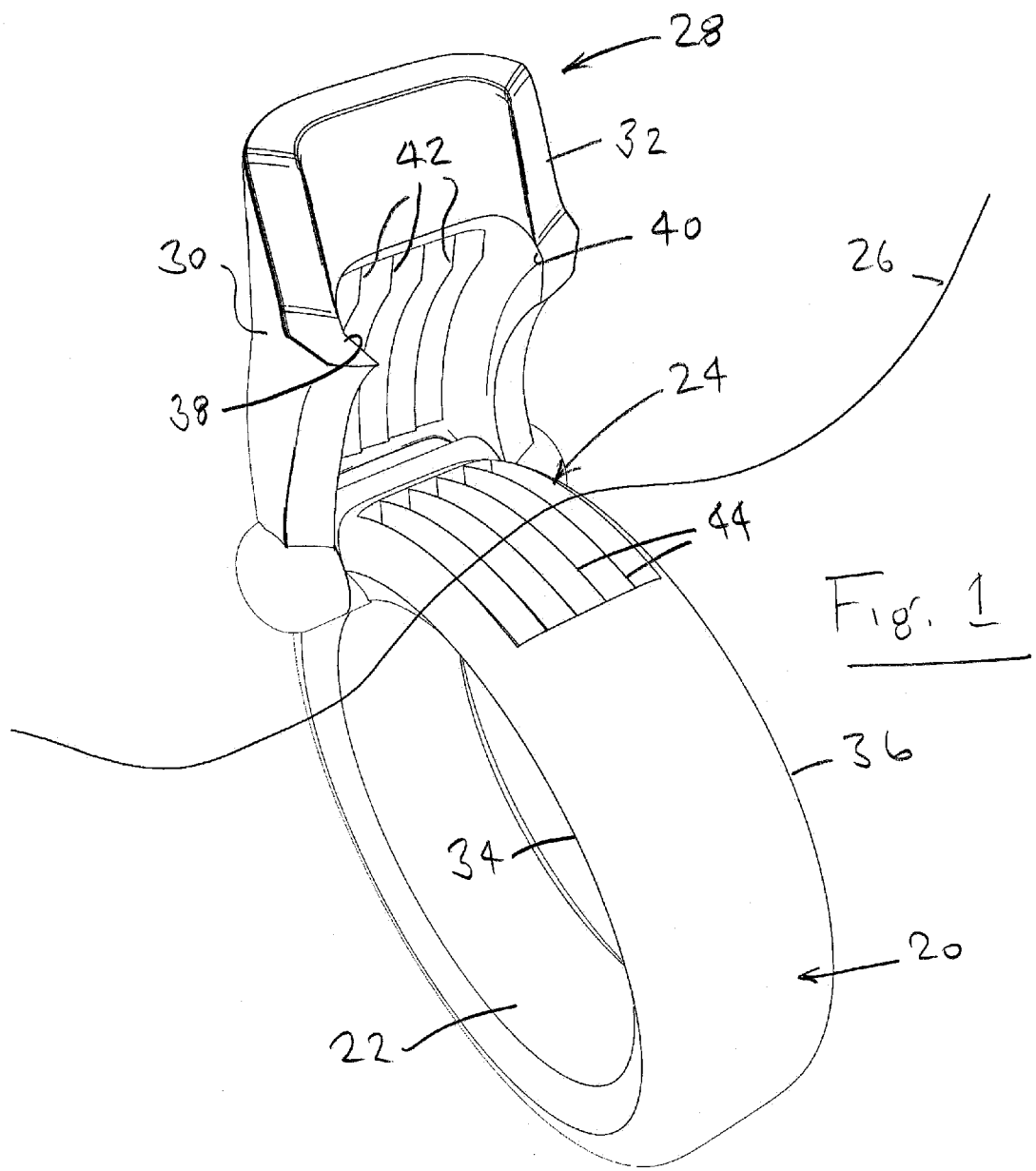
FIGS. 1 and 2 are perspective and side elevational views respectively of the dental floss gripper showing the clamp in its open position.
Figure 2:
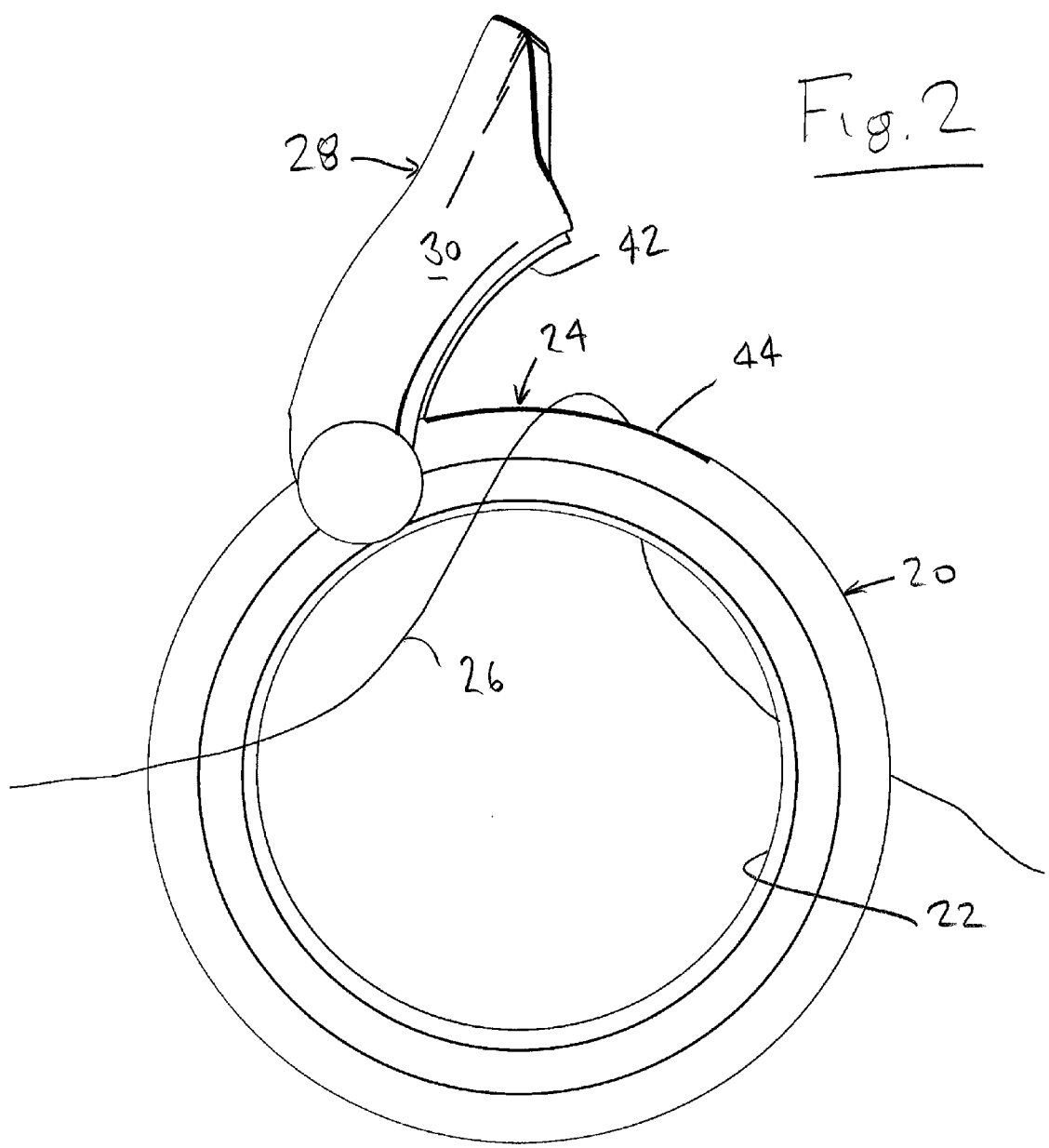
Figure 3:
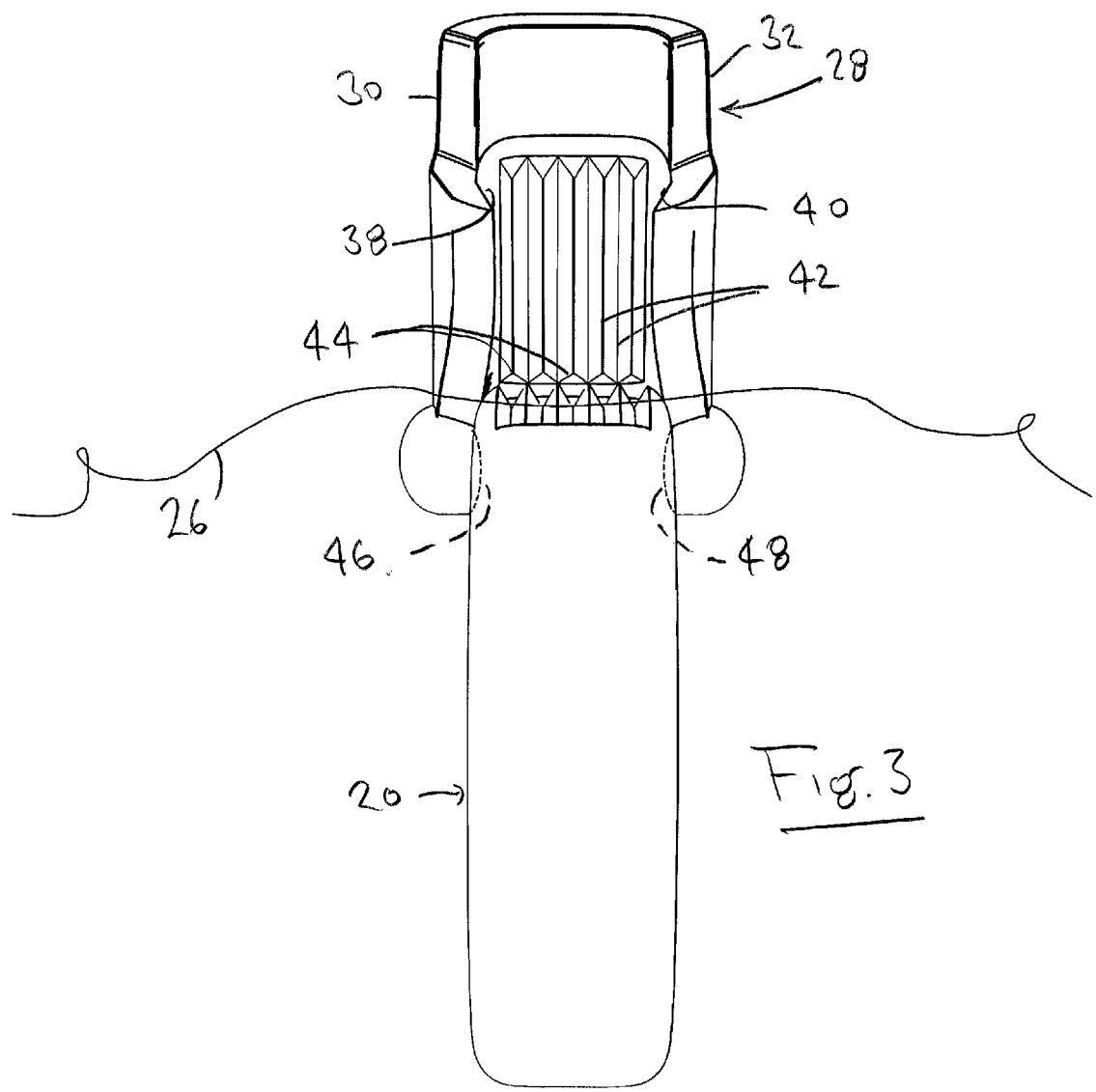
FIG. 3 is an elevational view from the right in FIG. 2.
Figure 4:
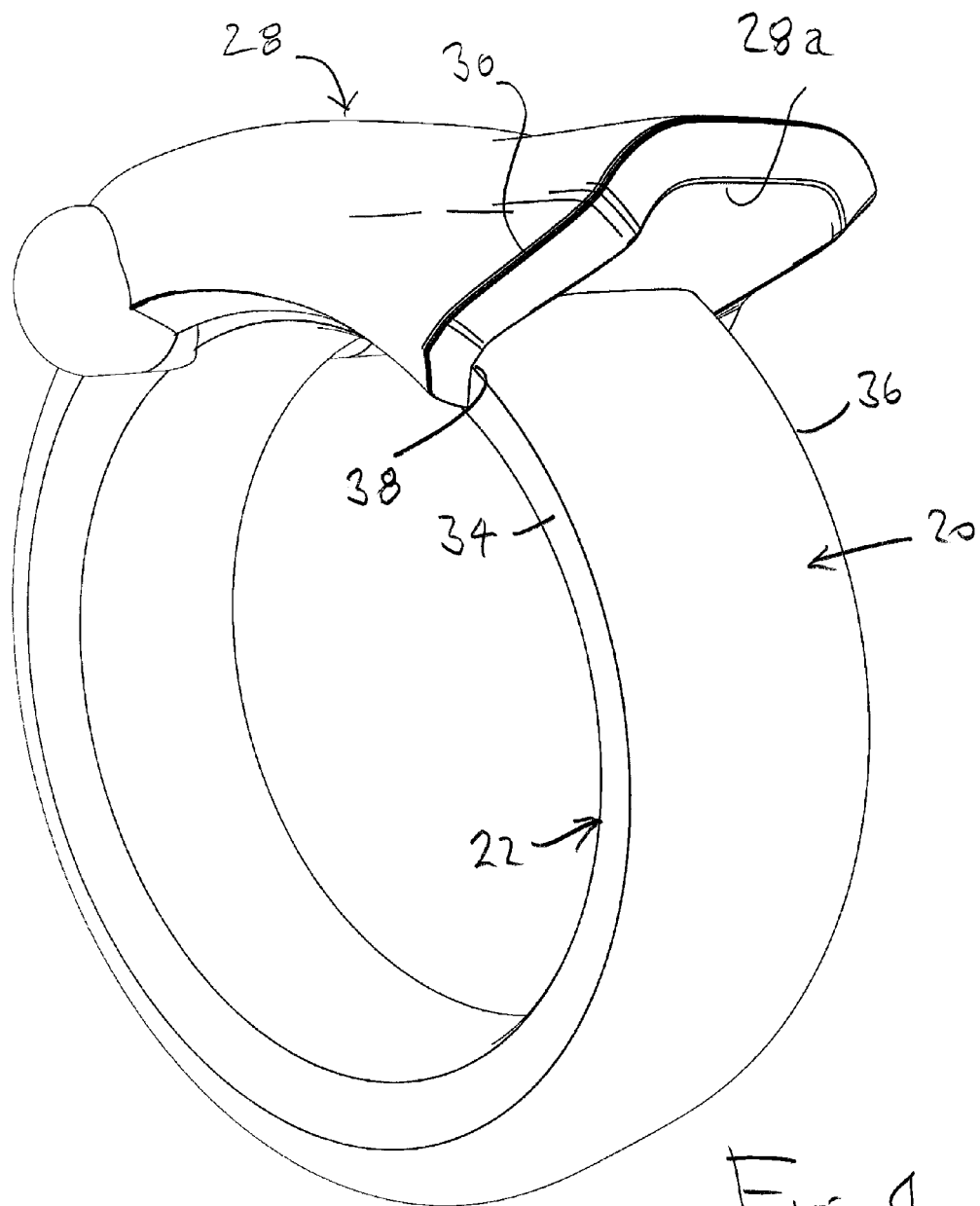
FIG. 4 is a perspective view showing the clamp in its closed position.

A clamp 28 is pivotally coupled to the base element for movement between the closed position in which it is shown in FIG. 4 in which the clamp overlies the outer surface portion 24 of the base element and an open position shown in FIGS. 1 to 3. The outer surface portion 24 of the base element 20 and the clamp have confronting surfaces which co-operate to clamp the length of dental floss 26 between the surfaces when the clamp is in its closed position. The clamp 28 and the base element 20 are configured so that the clamp releasably snap-fits to the base element in moving to its closed position. It can be seen that, in the open position, the length of dental floss 26 can be positioned between the confronting surfaces of the clamp and base element and removed after use.

In the embodiment shown in the drawings, the base element 20 is in the form of a ring sized so that the opening 22 can conveniently receive the finger of a user of the gripper. The internal diameter of the ring is preferably about 2 cm. The ring has an outer surface that is flat in cross-section.

Clamp 28 is generally channel-shaped in cross-section and curved in the longitudinal direction. The curvature of the clamp 28 matches the curvature of the ring 22. In the transverse direction, the channel-shape is dimensioned to fit over and embrace the surface portion 24 of the ring 22. The clamp has side walls 30 and 32 that closely fit over the corresponding side walls 34, 36 of the ring as best shown in FIG. 4. It can be seen that inner surface portions of the respective side walls 30, 32 of the clamp 28 are contoured to provide respective concave portions 38, 40 that fit relatively closely around the side wall portions 34, 36 of the ring. Portions 38, 40 are contoured and laterally dimensioned to snap-fit over the ring when the clamp is in its closed position.

Internally, the clamp 28 is provided with a series of longitudinal ribs 42 that are spaced laterally of the clamp. The ribs 42 are of triangular shape in cross-section so as to define a series of longitudinal edges that will mechanically engage the dental floss 26 when the clamp 28 is in its closed position. As best seen in FIG. 1, the surface portion 24 of the ring is provided with a corresponding series of similar longitudinal ribs 44 which co-operate with the ribs 42 when the clamp is in its closed position. Together, the longitudinal edges defined by the respective series of ribs interact to securely clamp the length of dental floss and guard against unwanted longitudinal movement thereof when the gripper is in use.

The clamp is pivotally coupled to the ring at its inner end by a pair of part-spherical formations 46, 48 (FIG. 3) that extend inwardly from opposite sides of the clamp and are received in corresponding recesses in opposite sides of ring 20. The formations 46, 48 define a virtual pivot axis for clamp 28.

Ring 22 and clamp 28 are molded from an appropriate plastic material.

FIG. 5 shows a dental floss gripper in accordance with the invention disposed on the index finger of a user with the clamp in an open position in FIG. 5(a) and in a closed position in FIG. 5(b). It will be appreciated that with the gripper positioned as shown in FIG. 5(a), the user can easily close the clamp simply by pressing down with his or her thumb. Conversely, the clamp can readily be opened by an upward "flicking" motion of the thumb from the position of the FIG. 5(b). As best seen in FIG. 4, a lip 28a is provided at the outer end of clamp 28 to facilitate this motion.

FIGS. 6(a) and 6(b) show the dental floss gripper of the invention in use. In this case, two grippers are used, one on the middle finger of each hand and the dental floss extends between the two hands and can be gripped between the index finger and thumb of each hand as best shown in FIG. 6(a). In FIG. 6(b), the dental floss is being used to clean the lower teeth and is held in a similar manner. It is of course possible that only one gripper might be used, with the other end of the dental floss being held by the fingers of the user.

It will of course be understood that the preceding description relates to a preferred embodiment of the invention and that many modifications are possible within the broad scope of the invention. Some of those modifications have been mentioned previously and others will be apparent to a person skilled in the art.

In the illustrated embodiment, the dental floss gripper is designed so that a length of dental floss extends transversely of the outer surface portion of the ring of the gripper. However, in an alternative embodiment, the gripper could be designed so that length of dental floss will extend longitudinally of the outer surface portion of the ring and through a gap between the ring and the clamp.

Another possible modification is to provide only one series of ribs either on the ring or on the clamp and to provide a roughened or other high-friction surface on the other of the ring and the clamp, against which the ribs can act. More broadly still, high-friction surface portions may be provided instead of ribs on both the ring and the clamp.

The clamp could be provided with a projection such as a button, lever or side tab to make it easier to flick upwardly on the clamp and move it to its open position. In either event, the intent is that the clamp can be operated single-handedly.

Finally, it is also possible that the gripper device of the invention could be provided internally with means for storing dental floss.

The invention claimed is:

1. A dental floss gripper comprising: a base element in the form of a ring sized to receive a finger of a user and having an outer surface extending around the ring, a portion of said surface being adapted for supporting a length of dental floss; and a clamp pivotally coupled to the base element for movement between a closed position in which the clamp overlies said outer surface portion of the base element, and an open position; said base element and said clamp having confronting surfaces which co-operate to clamp the length of dental floss therebetween when the clamp is in the closed position, the clamp and base element being configured so that the clamp releasably snap-fits to the base element in moving to said closed position and in its open position permits insertion and subsequent removal of a length of dental floss between said confronting surface; wherein the clamp has an arcuate shape that corresponds generally to the curvature of the ring and is pivoted at one end to the ring, the clamp being generally channel-shaped in cross-section and having opposite side walls which embrace opposite side portions of the ring when the clamp is in its closed position, the side walls of the channel and corresponding side portions of the ring being shaped to provide said snap-fitting of the clamp to the base element in moving to the closed position.

2. A dental floss gripper as claimed in claim 1, wherein at least one of the confronting surfaces of the ring and clamp have protuberant formations for mechanically gripping the dental floss.

3. A dental floss gripper as claimed in claim 2, wherein the formations comprise a series of ribs of generally triangular cross-section that extend longitudinally of the relevant confronting surface and are spaced transversely of that surface.

4. A dental floss gripper as claimed in claim 3, wherein the confronting surfaces of both the ring and the clamp are provided with respective series of ribs.

5. A dental floss gripper as claimed in claim 1, wherein the ring and clamp are made of a plastic material.

6. A dental floss gripper as claimed in claim 1, wherein the plastic material includes a silicone or latex additive to enhance the gripping effect between the ring and clamp and/or to enhance comfort of the ring in wear.

* * * * *